United States Patent [19]

Steer et al.

[11] 4,421,511
[45] Dec. 20, 1983

[54] FEMALE INCONTINENCE DEVICE

[75] Inventors: Peter L. Steer; John V. Edwards, both of East Grinstead, England

[73] Assignee: Craig Medical Products Limited, Sussex, England

[21] Appl. No.: 238,189

[22] Filed: Feb. 25, 1981

[30] Foreign Application Priority Data

Mar. 6, 1980 [GB] United Kingdom ............... 8007738
Oct. 15, 1980 [GB] United Kingdom ............... 8033222

[51] Int. Cl.³ ............................................. A61F 5/44
[52] U.S. Cl. ..................................... 604/329; 4/144.3
[58] Field of Search ................... 128/295, 760, 761; 4/144.1, 144.2, 144.3, 144.4; 604/327, 329, 346, 330, 331

[56] References Cited

U.S. PATENT DOCUMENTS

| 1,105,488 | 7/1914 | Clave | 128/295 |
|---|---|---|---|
| 2,483,079 | 9/1949 | Williams | 128/295 |
| 2,638,093 | 5/1953 | Kulick | 128/133 |
| 3,080,865 | 3/1963 | Vincent | 128/98 |
| 3,194,238 | 7/1965 | Breece | 128/295 |
| 3,349,768 | 10/1967 | Keane | 128/276 |
| 3,374,790 | 3/1968 | Mayhorne | 128/295 |
| 3,473,172 | 10/1969 | Friedman et al. | 4/144.3 |
| 3,512,185 | 5/1970 | Ellis | 4/110 |
| 3,528,423 | 9/1970 | Lee | 128/295 |
| 3,556,102 | 1/1971 | Davis | 128/295 |
| 3,613,122 | 10/1971 | Gross et al. | 4/144.4 |
| 3,646,929 | 3/1972 | Bonnar | 128/1 R |
| 3,661,155 | 5/1972 | Lindan | 128/295 |
| 3,683,914 | 8/1972 | Crowley | 128/285 |
| 3,776,235 | 12/1973 | Ratcliffe et al. | 128/295 |
| 3,864,759 | 2/1975 | Horiuchi | 128/295 |
| 3,995,329 | 12/1976 | Williams | 4/144.3 |
| 4,139,006 | 2/1979 | Corey | 128/127 |
| 4,194,508 | 3/1980 | Anderson | 128/295 |
| 4,198,979 | 4/1980 | Cooney et al. | 128/295 |
| 4,202,058 | 5/1980 | Anderson | 4/144.3 |
| 4,270,539 | 6/1981 | Michaud | 4/144.3 |

FOREIGN PATENT DOCUMENTS

| 18749 | 11/1980 | European Pat. Off. |  |
|---|---|---|---|
| 23942 | 2/1981 | European Pat. Off. | 128/295 |
| 895520 | 11/1953 | Fed. Rep. of Germany | 604/329 |
| 1766795 | 9/1971 | Fed. Rep. of Germany. |  |
| 1115727 | 5/1968 | United Kingdom. |  |
| 1144483 | 3/1969 | United Kingdom. |  |
| 1193261 | 5/1970 | United Kingdom. |  |
| 1422638 | 1/1976 | United Kingdom. |  |
| 1467144 | 1/1977 | United Kingdom. |  |

Primary Examiner—John D. Yasko
Assistant Examiner—J. L. Kruter
Attorney, Agent, or Firm—Lawrence S. Levinson; Stephen B. Davis

[57] ABSTRACT

A female incontinence device comprising an external resilient pad that makes sealing engagement with the user's anatomy that is external to the labia majora and a funnel having a rim dimensioned to engage that portion of the user's anatomy immediately surrounding the meatus of the urethra. The funnel is mounted to the pad, formed as part of the pad, or dimensioned to fit through an opening in the pad.

4 Claims, 8 Drawing Figures

FEMALE INCONTINENCE DEVICE

BACKGROUND OF THE INVENTION

There have been many prior proposals for devices to assist females who are afflicted with incontinence and among the major problems which are not yet completely solved are the following:
  (a) comfort to the wearer;
  (b) good sealing to preclude liquid escape;
  (c) minimizing impediment to movement of the wearer;
  (d) easy removability for cleaning or replacement.

There have been some proposals for devices to be worn entirely internally, and which assist the wearer in her own control of micturition as note Corey U.S. Pat. No. 4,139,006. Other devices which have been proposed are collection systems that are worn externally and are retained by the protrusion of some part of the device into the vagina as note, for example, Ratcliff et al. U.S. Pat. No. 3,776,235 and Linden U.S. Pat. No. 3,661,155. Breece in U.S. Pat. No. 3,194,238 discloses a female incontinence device having an open-ended tube 12 of bellows or accordion formation which is intended to seal with skin surfaces surrounding the urethral orifice. While liquid sealing may be satisfactory upon initial donning of such devices, movement by the user is likely to disturb the spatial relationship between the parts of the device and hence the sealing will become less effective. Once the patient loses confidence in the effectiveness of the sealing provided by the device, it is unlikely that the particular design of device will be acceptable to that patient. The sealing problem is exacerbated by the wide variations in size and topography of the relevant parts of the female body.

SUMMARY OF THE INVENTION

This invention is directed to a female incontinence device which includes an external resilient pad designed to make sealing engagement with that portion of the user's anatomy that is external to the labia majora and a funnel having a rim dimensioned so as to engage that portion of the user's anatomy which immediately surrounds the meatus of the urethra. The funnel is mounted to the pad, formed as part of the pad, or dimensioned to fit through an opening in the pad so that liquid discharged from the urethra passes into the funnel and then flows through a tube leading to a collection bag or bottle.

The devices of this invention have the advantage that there are two separate sealing regions, one provided by the pad and one by the funnel rim. By forming one or both of the pad and the funnel of flexible polyurethane elastomer, a close conformity with the shape of the confronting skin surface and consequent enhanced sealing is obtained.

In certain embodiments of this invention where the funnel is mounted or fits through an opening in the pad, the funnel can readily be removed and replaced, by the user, without the use of special measures or tools, and thus its cleaning or replacement can be easily accomplished. Also, in fitting an incontinence device to a user, a pad of appropriate size can be chosen and can be coupled to a funnel also of appropriate size. In this way it is possible to cater for a wide variety of anatomical sizes without the need to stock a vast number of complete incontinence devices.

The female incontinence device of the invention can be varied to accurately fit different users by choosing a mount of appropriate height and angle to the general plane of the pad, and the resilient deformable characteristic of the material of the funnel enhances the possibility of a good seal being achieved by the funnel rim.

DETAILED DESCRIPTION OF THE INVENTION

Figure 1:
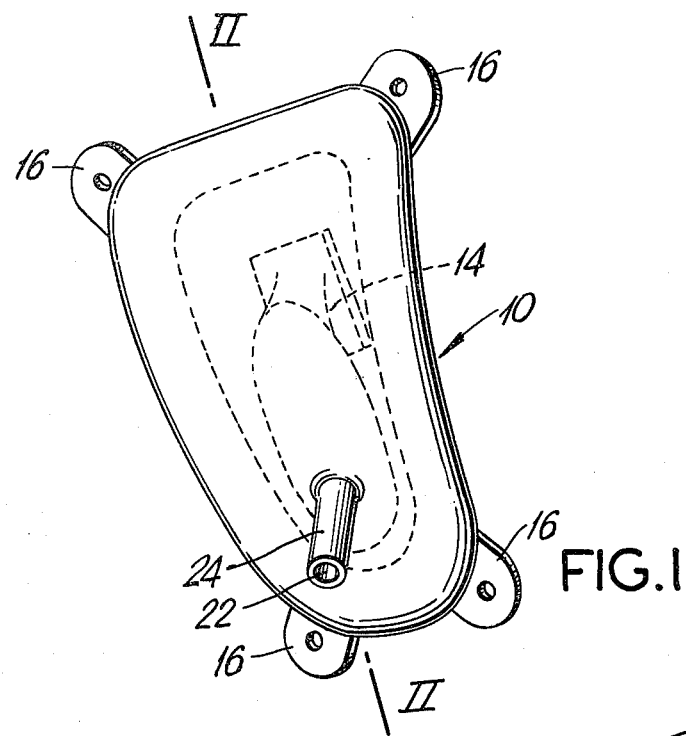
FIG. 1 is a schematic perspective external view of a pad portion of a female incontinence device according to one embodiment of the invention.
Figure 2:
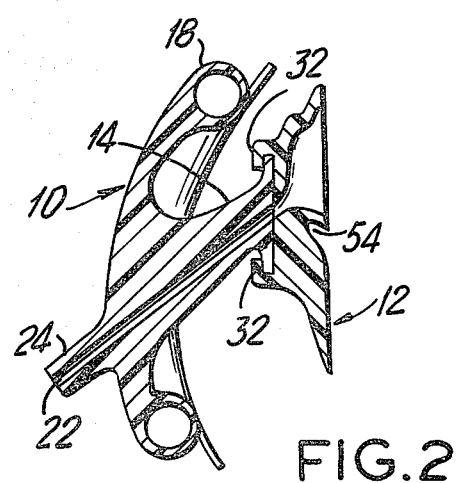
FIG. 2 is a schematic vertical central section through the device of FIG. 1 taken along line II—II.
Figure 4:
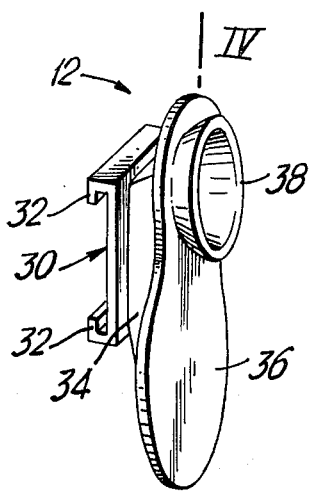
FIG. 4 is a schematic perspective of one form of funnel useable with the device shown in FIGS. 1 to 3.
Figure 5:
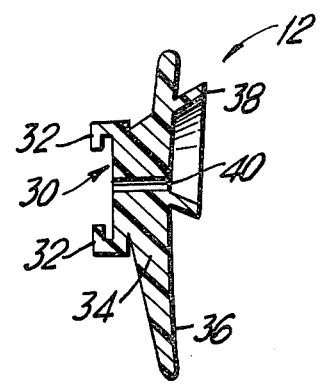
FIG. 5 is a schematic vertical section through the funnel shown in FIG. 4 taken along line IV—IV.

The female incontinence device illustrated in FIGS. 1 to 6 has two main parts, a pad 10 and a funnel 12, FIGS. 2 and 4. The pad includes a mount or pedestal 14. The mount supports the funnel in a snap-on and readily detachable manner. The pad 10 has loops 16, or clips or like members, whereby it can be attached to straps and the belt which hold it on the user, with the pad covering the genital area.

Figure 3:
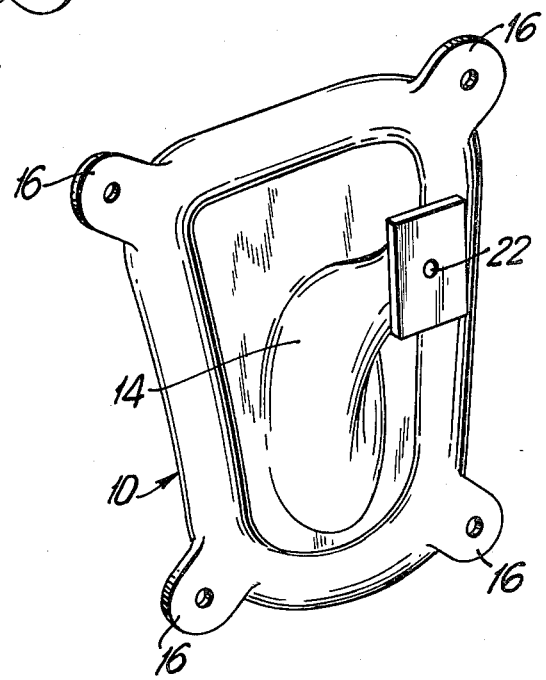
FIG. 3 is a schematic perspective internal view of the device of FIGS. 1 and 2 showing one form of mount but with the funnel omitted.
Figure 3A:
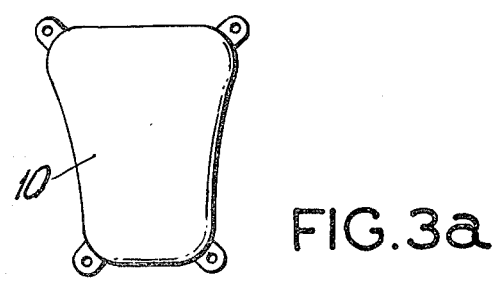
FIG. 3a is a schematic view of a pad portion of the device of FIG. 3.
Figure 6:
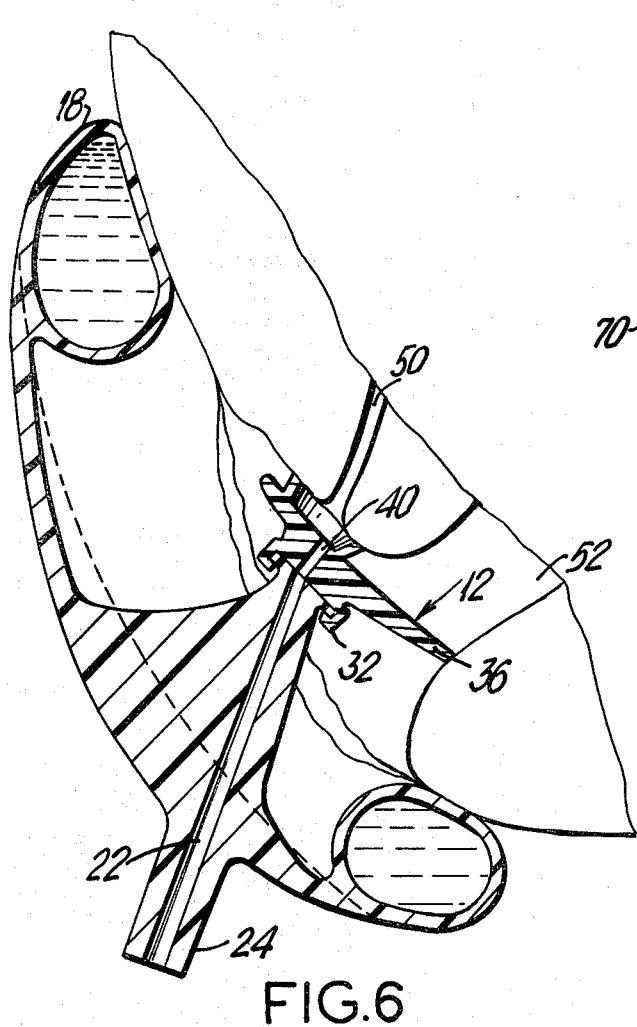
FIG. 6 is a schematic vertical section of the device shown in FIGS. 1 to 5 in position on a user.

The pad 10 as illustrated in FIG. 6 has a hollow tubular rim that forms a sealing cuff 18 with the adjacent area of the skin of the wearer. The cuff may be gas or liquid filled or may be inflatable at will. For simplicity, it is generally preferred to have the hollow tubular rim 18 contain a liquid such as a silicone fluid. The pad 10 is shaped, seen in front view, as a rectangle modified in that it has incurving sides and is slightly wider at the top than at the bottom, as seen in FIG. 3a. The central part of the pad 10 supports the mount 14 which projects towards the wearer and has a central hole 22 therethrough. This hole leads to a drain tube 24 connected to the pad 10. The mount may be permanently fixed to the pad 10, or may be fixed therein by a snap-fit connection.

The funnel 12 is preferably made of an impact-absorbing elastomeric polyurethane material which is deformable under light pressure and tends to spring back to its original position. It may be molded as one piece from said material and a preferred form is illustrated in FIGS. 4 and 6. The funnel comprises a base portion 30 having parallel grooves 32 by which it can be snapped onto the head of the mount 14, a support web 34, a generally flat gasket 36, and a funnel wall 38 arising out of the flat gasket 36. A hole 40 extends from the interior of the funnel wall to an orifice on the base 30 which is in registry with the orifice of the hole 22 through the mount 14. The device when worn by a female is worn in the manner illustrated in FIG. 6. The funnel 12 is snapped onto the mount 14. The deformable lips of the funnel wall 38 immediately surround the orifice (meatus) of the urethra 50 and the gasket 36 largely obturates the vagina 52. The hollow rim 18 engages the user's skin externally, and provides a "back-up" seal in case any urine should fail to follow the intended path which of course is into the funnel 12, through the hole 40, through the hole 22 and into the drain tube 24.

Figure 7:
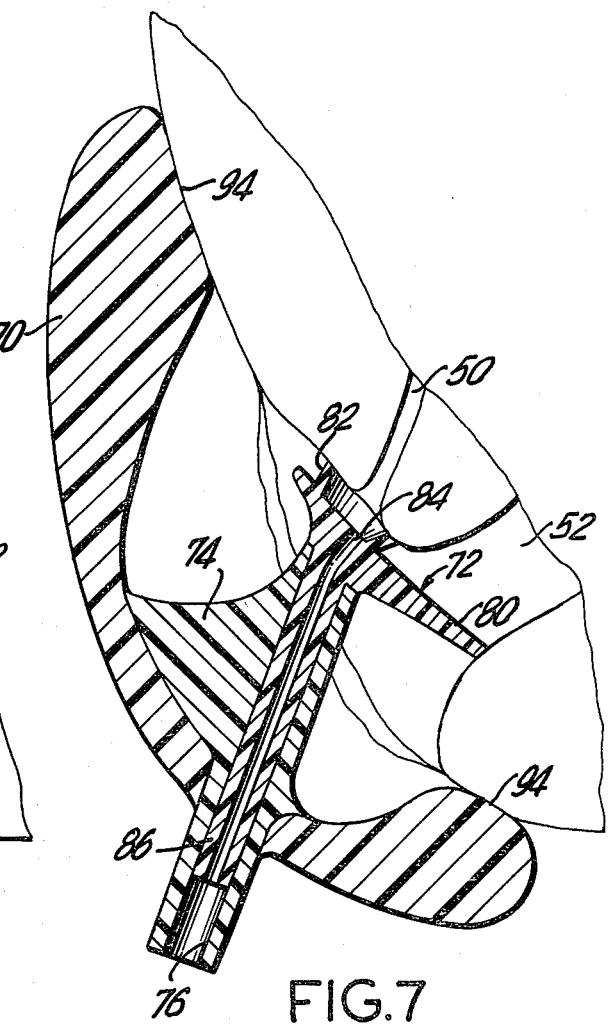
FIG. 7 is a schematic vertical section of a female incontinence device according to another embodiment of the invention in position on a user.

Another embodiment of the female incontinence device of this invention is illustrated in FIG. 7. The device has three main parts, namely a pad 70, a funnel 72, and a funnel support 74 fixed to or integral with pad 70. The pad 70 can have loops 16 in the same manner as pad 10 and is of the same rectangular configuration as pad 10. Pad 70 can also be constructed with a hollow tubular rim.

The funnel 72 is preferably made of an impact absorbing elastomeric polyurethane material which is deformable under light pressure but tends to spring back to its original position. It may be molded as one piece from said material. The funnel 72 comprises a generally flat gasket 80, a funnel wall or rim 82 arising out of flat gasket 80, and a downwardly extending tube 86. Gasket 80 and rim 82 may be identical in shape to gasket 36 and rim 38 of funnel 12 described above. A hole 84 extends from the interior of the funnel wall to the tube 86. The tube 86 is pushed into a complementary hole 76 in funnel support 74. Tube 86 and support 74 could be molded from synthetic plastics material. The respective dimensions of the tube 86 and hole 76 in the support 74 are such that the tube 86 can be adjusted manually in its longitudinal position in the support 74 but once so adjusted, is held firmly therein by friction. As an alternative, not illustrated, the tube 86 or the support 74 could be provided with small projections, e.g., of rounded configuration, and these could cooperate with a complementary recess in the wall of the support or tube as the case may be. Consequently, by engaging a chosen one of the projections in the recess, the wearer, before donning the device, could adjust the position of the funnel rim 82 relative to the pad 70 and thus achieve the optimum sealing relationship of these parts with the relevant parts of her own body. That is to say, optimum sealing relationships between on the one hand the rim 82 and the region surrounding the meatus and on the other hand the pad region 94 and the flesh external to the labia mafora can be simultaneously achieved.

When the device of this embodiment is in place on the body of user as illustrated in FIG. 7, the deformable rim 82 of the funnel immediately surrounds the orifice (meatus) of the urethra 50 and the gasket 80 largely obturates the vagina 52. The marginal region 94 of the pad 70 engages the user's skin externally, and provides a "back-up" seal in case any urine should fail to follow the intended path which, of course, is into funnel 72, through hole 84 in tube 86, and out through hole 76.

In either embodiment of the invention, the flat gasket 36 or 80 may have a small depression adjacent to the funnel wall leading to a small hole. Such a small depression 54 (but not the hole) is illustrated in FIG. 2. This arrangement allows any secretions from the vagina which collect on the gasket to pass into the funnel.

The incontinence devices of this invention may be held in position on the body by straps and a belt attached to loops 16 or by means of a specially designed garment. Alternatively, a portion of the surface of pad 10 or pad 70 which contacts the surface of the skin may be coated with a medical grade adhesive.

A particularly preferred material for the funnel 12 and the funnel 72, and which may also be used for the pad 10, the pad 70 and the flange support 74, is an impact absorbing polyurethane elastomer commercially available under the name Sorbothane (BTR Limited, London, England).

An important advantage of the female incontinence devices of this invention is that they provide a "double seal", that is to say, one seal is created by the funnel wall around the urethral orifice and a second seal is created by the tubular rim around the genital area. In addition, variations in anatomical size and shape do not affect the effectiveness of the second seal and can be catered for as regards the first seal by replacement of the funnel. The hygiene of the device, particularly of the embodiment shown in FIGS. 1 to 6, is of a high order because the funnel can be easily removed and cleaned or discarded. It may be replaced if appropriate, or a new funnel may be fitted.

It is envisaged that a stock of funnels of different sizes and shapes would be carried to suit different women, and one of these could be readily fitted on mount 14 or slid into support 74.

What is claimed is:

1. A female incontinence device comprising an external resilient pad having a peripheral portion in the form of a hollow tube, said tube filled with a liquid silicone fluid, the tube being designed to make sealing engagement with that portion of the user's anatomy which is external to the labia majora, a mount forming part of the pad, and a funnel carried by the mount and shaped and dimensioned so that a rim thereof can engage that portion of the user's anatomy which immediately surrounds the meatus of the urethra.

2. A device according to claim 1 wherein the funnel is integral with a generally flat gasket member positioned to substantially close off the vaginal opening of a user of the device.

3. A device according to claim 1 wherein the mount is integral with the pad and has a head constructed for ready attachment of the funnel thereto.

4. A device according to claim 1 wherein at least the funnel is of an impact absorbing polyurethane elastomer.

* * * * *